United States Patent
Sun et al.

(10) Patent No.: US 10,099,002 B2
(45) Date of Patent: Oct. 16, 2018

(54) SYSTEMS AND METHODS FOR PARALLEL CHANNEL MICROFLUIDIC SEPARATION

(71) Applicant: The Charles Stark Draper Laboratory, Inc., Cambridge, MA (US)

(72) Inventors: Hoi-Cheong Steve Sun, Tampa, FL (US); Jason Oliver Fiering, Boston, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 446 days.

(21) Appl. No.: 14/815,501

(22) Filed: Jul. 31, 2015

(65) Prior Publication Data
US 2016/0030660 A1 Feb. 4, 2016

Related U.S. Application Data

(60) Provisional application No. 62/031,662, filed on Jul. 31, 2014.

(51) Int. Cl.
*B01D 17/12* (2006.01)
*A61M 1/36* (2006.01)
*B01D 21/28* (2006.01)

(52) U.S. Cl.
CPC ........ *A61M 1/3693* (2013.01); *A61M 1/3678* (2014.02); *A61M 1/3687* (2013.01); *B01D 21/283* (2013.01); *B01D 2221/10* (2013.01)

(58) Field of Classification Search
CPC ............. G01N 15/1404; G01N 21/453; G01N 2015/142; G01N 21/00; G01N 1/4077;
(Continued)

(56) References Cited

U.S. PATENT DOCUMENTS 8,083,068 B2 12/2011 Kaduchak et al.
2004/0005582 A1 1/2004 Shipwash
(Continued)

FOREIGN PATENT DOCUMENTS

EP 0 914 184 A1 5/1999
EP 1 809 399 B1 8/2009
(Continued)

OTHER PUBLICATIONS

International Preliminary Report on Patentability dated Sep. 17, 2015 in PCT App No. PCT/US2014/022701.
(Continued)

*Primary Examiner* — Walter D. Griffin
*Assistant Examiner* — Cameron J Allen
(74) *Attorney, Agent, or Firm* — Christopher J. McKenna; Foley & Lardner LLP

(57) ABSTRACT

The present disclosure describes a system and method for microfluidic separation. More particularly, the disclosure describes a system and method for the purification of a fluid by the removal of undesired particles. The device includes microfluidic separation channels that include multiple outlets. The device also includes isolation slots positioned between each of the microfluidic separation channels. The device's base includes multiple acoustic transducers which in some implementations are configured to protrude into the isolation slots. The acoustic transducers are configured to generate aggregation axes within the separation channels, which are used to separate out undesired particles.

15 Claims, 9 Drawing Sheets

(58) Field of Classification Search
CPC ............ G01N 2015/0288; B01D 57/02; B01D 17/00; B01D 17/12; B01D 21/283; B01D 2221/10; A61M 1/3472; A61M 1/3687; A61M 1/3678; A61M 1/3693

See application file for complete search history.

(56) References Cited

U.S. PATENT DOCUMENTS

| | | |
|---|---|---|
| 2008/0181828 A1 | 7/2008 | Kluck |
| 2008/0217259 A1* | 9/2008 | Siversson ............ A61M 1/3693 436/177 |
| 2010/0006501 A1 | 1/2010 | Laurell et al. |
| 2010/0078384 A1 | 4/2010 | Yang |
| 2013/0043170 A1 | 2/2013 | Rose et al. |
| 2013/0048565 A1 | 2/2013 | Fiering et al. |
| 2014/0209542 A1 | 7/2014 | Spain et al. |
| 2016/0008532 A1* | 1/2016 | Fiering ................ A61M 1/3693 210/666 |

FOREIGN PATENT DOCUMENTS

| | | |
|---|---|---|
| EP | 2 145 687 A1 | 1/2010 |
| EP | 2 352 570 A2 | 8/2011 |
| WO | WO-02/12896 | 2/2002 |
| WO | WO-02/29400 | 4/2002 |
| WO | WO-2006/032703 | 3/2006 |

OTHER PUBLICATIONS

U.S. Notice of Allowance on U.S. Appl. No. 14/168,822 dated Aug. 3, 2016.
U.S. Notice of Allowance on U.S. Appl. No. 14/168,822 dated Mar. 7, 2016.
U.S. Office Action on U.S. Appl. No. 13/598,401 dated May 20, 2016.
U.S. Appl. No. 13/598,401, filed Aug. 29, 2012.
U.S. Appl. No. 14/168,822, filed Jan. 30, 2014.
International Preliminary Report on Patentability dated Mar. 13, 2014 in PCT Application No. PCT/US2012/052886 (10 pages).
International Search Report and Written Opinion in PCT/US2014/022701 dated Jul. 18, 2014.
International Search Report and Written Opinion dated Dec. 11, 2012 in PCT Application No. PCT/US2012/052886.
U.S. Non Final Office Action on U.S. Appl. No. 13/598,401 dated Jan. 2, 2015.
U.S. Office Action in U.S. Appl. No. 13/598,401 dated Jul. 1, 2015.

* cited by examiner

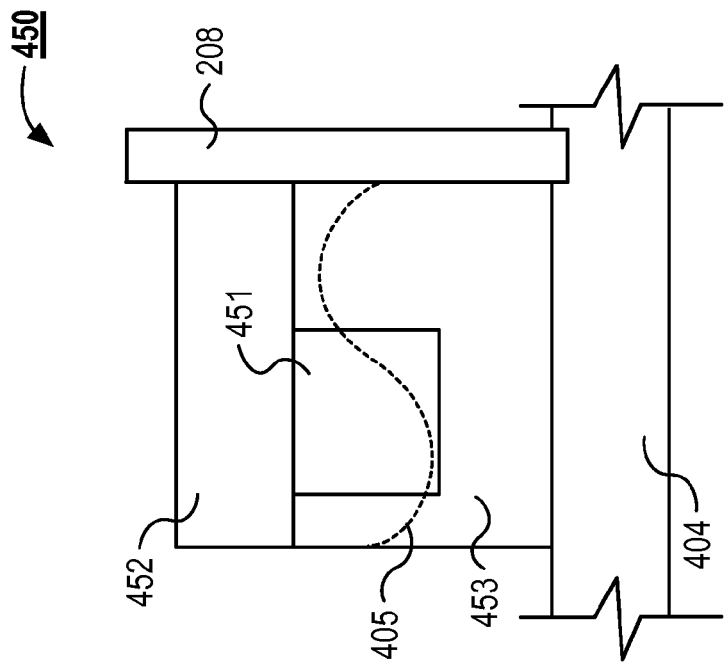
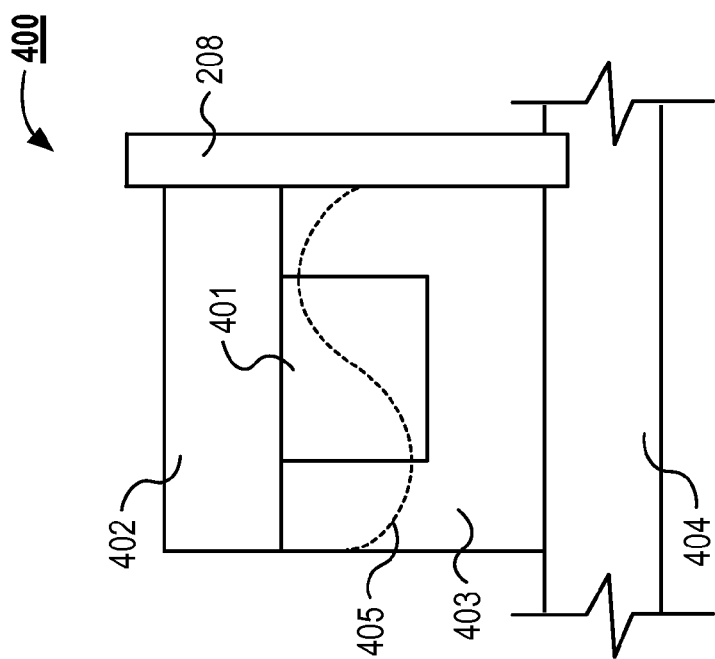

SYSTEMS AND METHODS FOR PARALLEL CHANNEL MICROFLUIDIC SEPARATION

CROSS REFERENCE TO RELATED CASES

This application claims priority to U.S. Provisional Patent Application No. 62/031,662 filed on Jul. 31, 2014 and titled "SYSTEMS AND METHODS FOR PARALLEL CHANNEL MICROFLUIDIC SEPARATION," which is herein incorporated by reference in its entirety.

BACKGROUND

The concept of blood cleansing and separation has been tried previously without success. Previous blood cleansing concepts have included laboratory scale methods of centrifugation, capillary electrophoresis, liquid chromatography, field flow fractionation, and liquid-liquid extraction. These devices have failed to deliver continuous flow cleansing devices. In additional to often discarding large portions of the blood, current cleansing devices may rely on: diluents, sheath flow, controlled solution conductivity, costly microfabricated on-chip materials, and toxic additives.

SUMMARY OF THE DISCLOSURE

According to one aspect of the disclosure a fluid cleansing device includes a plastic substrate. The substrate defines a plurality of microfluidic separation channels. Each of the microfluidic separation channels includes an upstream portion and a downstream portion. The upstream portion includes an inlet and the downstream portion includes a first outlet and at least a second outlet. The substrate also defines one or more isolation slots. One of the one or more isolation slots is positioned between each of the plurality of microfluidic separation channels. The device also includes a base substrate that is coupled to the plastic substrate. The base substrate includes one or more acoustic transducers. Each of the one or more acoustic transducers are coupled to a wall of one of the separation channels.

In some implementations, the first outlet of each of the plurality of microfluidic separation channels is positioned substantially along a longitudinal axis of the respective microfluidic separation channel. The second outlet of each of the plurality of microfluidic separation channels is positioned adjacent to a wall of the respective microfluidic separation channel. In some implementations, each of the one or more acoustic transducers protrude perpendicular to a face of the base substrate and into a respective one of the one or more isolation slots.

In some implementations, each of the plurality of microfluidic separation channels also include a first wall that has a first thickness and a second wall opposite the first wall that has a second thickness. In some implementations, the first thickness and the second thickness are equal to $c_s(f)/4f$, or an odd multiple thereof, where $c_s(f)$ is a frequency dependent speed of a shear wave through the plastic.

In other implementations, the second thickness is different than the first thickness. In some implementations, the first thickness is about $c_w(f)/4f+d$, the second thickness is about $c_w(f)/4f-d$, and a lateral width of each of the of microfluidic separation channels is about $c_f/2f$, where $c_w$ is an odd multiple of an acoustic velocity of an acoustic wave in the plastic substrate, $c_f$ is an acoustic velocity of the acoustic wave in a fluid flowing through each of the plurality of microfluidic separation channels, f is an operating frequency of the acoustic wave, and d is a width increment defined by $c_f/16f<d<c_f/4f$.

In some implementations, each of one or more isolation slots run substantially the entire length of the plurality of microfluidic separation channels. Each of one or more isolation slots can also run substantially parallel to the plurality of microfluidic separation channels. The one or more isolation slots each have a height equal to a thickness of the plastic substrate.

In some implementations, the device includes a manifold that is configured to distribute a fluid to the inlet of each of the plurality of microfluidic separation channels. The manifold can include a biomimetic network of branching channels.

According to another aspect of the disclosure, a method includes providing a fluid cleansing device. The fluid cleansing device includes a plastic substrate defining a plurality of microfluidic separation channels. Each of the microfluidic separation channels includes an upstream portion and a downstream portion. The upstream portion includes an inlet and the downstream portion includes a first outlet and a second outlet. The substrate also includes one or more isolation slots positioned between each of the plurality of microfluidic separation channels. The method also includes flowing a fluid that includes particles through the plurality of microfluidic separation channels. The particles are directed, with an acoustic wave, toward a first aggregation axis of each of the plurality of microfluidic separation channels.

In some implementations, the method also includes applying the acoustic wave to each of the plurality of microfluidic separation channels with a different acoustic transducer. Each of the different acoustic transducers is positioned in a respective isolation slot. The method also includes collecting the particles at the first outlet.

In some implementations, each of the plurality of microfluidic separation channels also include a first wall that has a first thickness, and a second wall opposite the first wall that has a second thickness. The first thickness and the second thickness are equal to $c_s(f)/4f$, or an odd multiple thereof, where $c_s(f)$ is a frequency dependent speed of a shear wave through the plastic. In other implementations, the second thickness is different than the first thickness.

In some implementations, the method also includes flowing the fluid into the inlet of each of the plurality of microfluidic separation channels through a manifold.

According to another aspect of the disclosure a separation device includes a plastic substrate that defines a first separation channel. The first separation channel includes an upstream portion and a downstream portion. The upstream portion includes an inlet, and the downstream portion includes a first outlet positioned along a first wall and a second outlet positioned along a second wall. The thickness of the first wall is different than the thickness of the second wall.

In some implementations, the device also includes a base substrate coupled to the plastic substrate. The base substrate includes an acoustic transducer configured to project a standing wave into the first separation channel. In some implementations, the plastic substrate also includes a second separation channel adjacent to the first separation channel. The plastic substrate also includes an isolation slot positioned between the second separation channel and the first separation channel.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar and/or structurally similar elements throughout the various drawings. The drawings are not necessarily to scale, emphasis instead being placed upon illustrating the principles of the teachings. The drawings are not intended to limit the scope of the present teachings in any way. The system and method may be better understood from the following illustrative description with reference to the following drawings in which:

FIG. 4A illustrates a cross-sectional view of an example microfluidic flow chamber with symmetrical walls as can be used in the system illustrated in FIG. 1.

FIG. 4B illustrates a cross-sectional view of an example microfluidic flow chamber with asymmetrical walls as can be used in the system illustrated in FIG. 1.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

Figure 1:
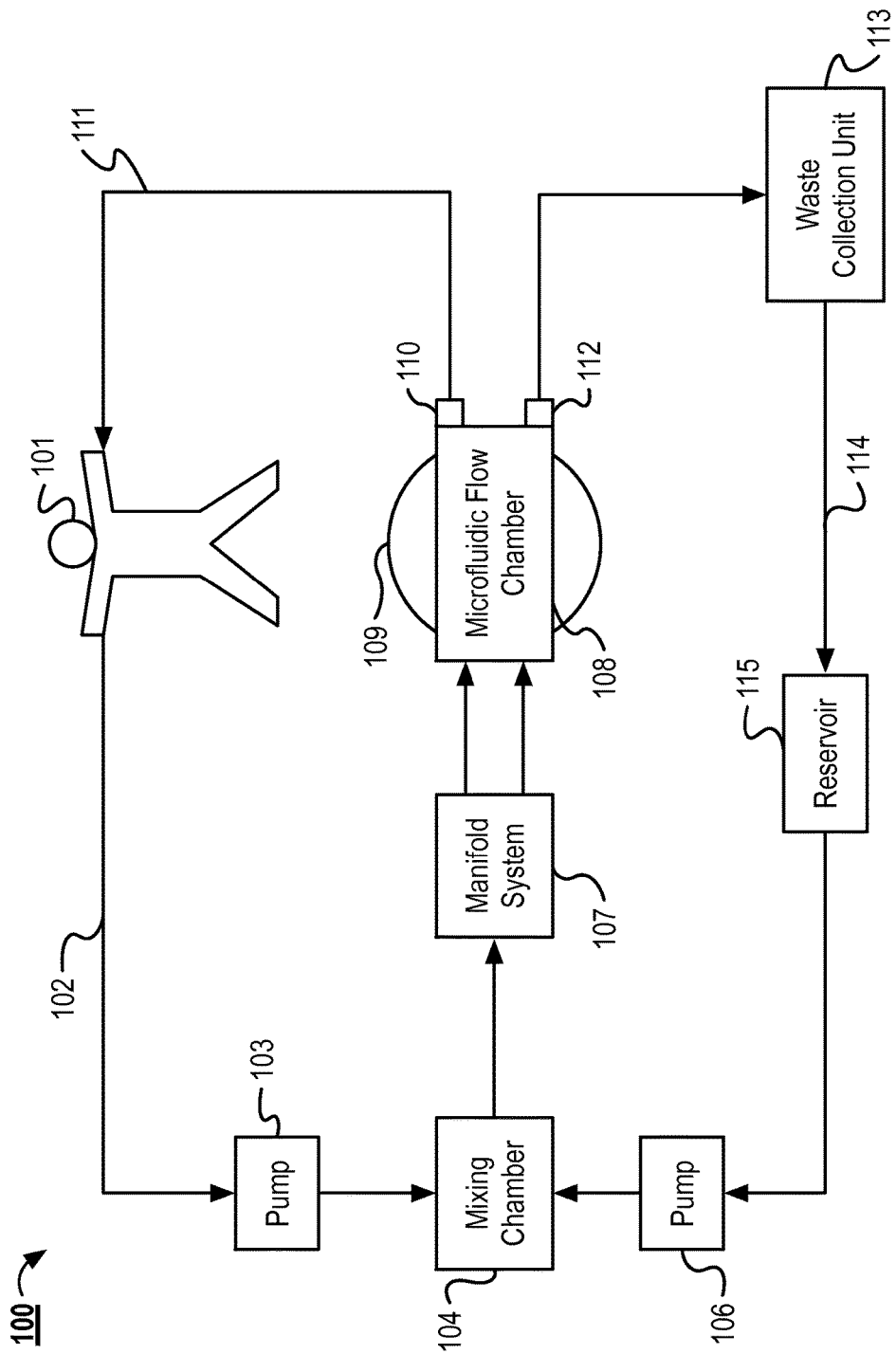
FIG. 1 illustrates an example system for separating contents of a fluid.

FIG. 1 illustrates an example system 100 for separating the contents of a fluid. In the system 100, blood (or another fluid to be processed) is removed from a patient via an intravenous line 102. The blood is then pumped to a mixing chamber 104 by a pump 103. In the mixing chamber 104, capture particles are mixed with the blood. The components of the capture particles are stored in a reservoir 115. From the reservoir 115, the capture particles are pumped by a pump 106 into the mixing chamber. From the mixing chamber 104, the blood and capture particles enter a manifold system 107. The manifold system 107 distributes the blood and capture particles to a plurality of separation channels contained within the microfluidic flow chamber 108. The microfluidic flow chamber 108 includes one or more piezoelectric acoustic transducers 109. The acoustic waves generated by the acoustic transducers 109 are used to funnel the contents of the blood and capture particles to specific outlets of the separation channels.

As the blood flows through the microfluidic flow chamber 108, the cleansed blood flows to a first outlet 110. After exiting the first outlet 110, the cleansed blood returns to the patient 101, via a second intravenous line 111. The capture particles and other waste material removed from the blood exit the microfluidic flow chamber 108 via a second outlet 112. The waste material and capture particles enter a waste collection unit 113. In the waste collection unit 113, the capture particles are separated from the waste material. Once separated, the waste material is discarded and the capture particles are returned to the reservoir 115 by tubing 114. Once returned to the reservoir 115, the capture particles are reused in the system to remove additional waste material from whole blood as it continues to flow through the system 100.

The system 100, as illustrated, includes a pump 103 for moving blood from the patient 101 to the mixing chamber 104. In some implementations, the pump operates continuously, while in other implementations the pump works intermittently, and only activates when the level of whole blood in the mixing chamber 104 or manifold falls below a set threshold. In some implementations, the flow rate of the pump is configurable, such that the rate the blood exits the patient can be configured to be faster or slower than if no pump was used. In yet other implementations, no external pump is required. In this example, the blood is transported to the mixing chamber 104 by the pressure generated by the patient's own heart. In some implementations, flow or pressure is monitored in the network, and these measurements in turn control the pump. Example pumps can include, but are not limited, to peristaltic pumps, impeller pumps or any other pump suitable for flowing blood.

As illustrated in the system 100, capture particles are also pumped into the mixing chamber. In some implementations, the capture particles are polystyrene beads or liposomes encapsulating an acoustically active fluid. The capture particles are described in greater detail below. A pump 106 pumps the capture particles from a reservoir 115 to the mixing chamber 104. In the mixing chamber 104, affinity particles embedded within the surface of the capture particles bind to undesired particles, cells, or toxins to be removed from the blood.

As illustrated in FIG. 1, the capture particles are injected into the mixing chamber 104. In other implementations, the capture particles are injected into the manifold system 107 or directly into the separation channels of the microfluidic flow chamber 108. In some implementations, the system 100 does not use capture particles. In these implementations, the component of the fluid to be cleansed may be intrinsically acoustically active. For example, cells or other objects may have an acoustic contrast factor sufficiently different than that of the blood or other fluid and are therefore "acoustically active." These cells or other objects can be directed with the acoustic transducer 109.

As illustrated in system 100, the blood containing undesirable particles and the capture particles enter the mixing chamber 104. In some implantations, the contents of the mixing chamber are continuously agitated to improve distribution of the capture particles throughout the blood and undesirable particles such that the capture particles bind to the undesirable particles. In some implementations, anticoagulants or blood thinners are introduced into the mixing chamber 104 to assist the blood as it flows through the system 100. In some implementations, the mixing chamber 104 contains a heating element for warming the contents of the mixing chamber 104.

The contents of the mixing chamber 104 then flow into the manifold system 107, as illustrated by system 100. The manifold system 107 flows the blood, undesirable particles, and capture particles into the inlets of the plurality of separation channels of the microfluidic flow chamber 108. In some implementations, multiple microfluidic flow chambers described herein are stacked to process relatively large volumes of blood or other fluids. The manifold system 107 distributes the blood to each of the separation channels of the stacked microfluidic flow chambers. In some implementations, the manifold system 107 is configured to distribute shear sensitive fluids, such as blood, to each of the separation channels without damaging the shear sensitive fluids. In some implementations, the manifold system 107 is also configured to receive the shear sensitive fluid from the microfluidic flow chamber 108 after the fluid has flowed through the microfluidic flow chamber 108. The manifold can include gradual curving channels rather than right angles. In some implementations, the channels within the manifold mimic vascular channels. For example, the channels split at bifurcations. After a bifurcation the size of the channel is reduced according to Murray's Law. In some implementations, the manifold includes trunk and branch channels, where supply channels flowing to each of the microfluidic flow chambers branch from a main supply trunk. Additional information regarding the biomimetic manifold system 107 can be found in U.S. patent application Ser. No. 13/736,685, titled Compact Hydraulic Manifold Structure for Shear Sensitive Fluids, which is incorporated herein by reference in its entirety.

In the system 100, the microfluidic flow chamber 108 contains a plurality of separation channels. The microfluidic flow chamber 108 and separation channels are described further in relation to FIGS. 2A-5. The capture particles and undesirable particles are driven with standing acoustic waves to outlets. In other implementations, the acoustic wave is activated intermittently. In some implementations, the separation occurs during a single stage, while in other implementations, the separation occurs over a plurality of stages. In some implementations, the microfluidic flow chamber is disposable.

As show in the illustrations of system 100, the microfluidic flow chamber 108 sits atop an acoustic transducer 109. In some implementations, the system 100 contains a single acoustic transducer 109, while in other implementations the system 100 contains a plurality of acoustic transducers 109. Configurations illustrating multiple acoustic transducers 109 are described further in relation to FIGS. 2A-5.

In some implementations, the acoustic transducer 109 is glued to the microfluidic flow chamber 108. In other implementations the microfluidic flow chamber 108 is clamped to the acoustic transducer 109 so the microfluidic flow chamber may easily be removed from the system. In other implementations the adhesive material connecting the acoustic transducer 109 to the microfluidic flow chamber 108 is removable, for example by heating the adhesive.

The acoustic transducer 109 imposes a standing acoustic wave on the separation channels of the microfluidic flow chamber 108 transverse to the flow of the fluid within the microfluidic flow chamber 108. The standing acoustic waves are used to drive fluid constituents towards or away from the walls of the separation channels or other aggregation axes.

More particularly, the dimensions of the separation channels are selected based on the wavelength of the imposed standing wave such that pressure nodes are generated in each of the separation channels. The capture particles are driven to different positions within the separation channels based on the sign of their acoustic contrast factor at a rate which is proportional to the magnitude of their contrast factor. Capture particles or other elements with a positive contrast factor (e.g. the formed elements of blood) are driven towards the pressure nodes within the interior of the separation channel. In contrast, elements with a negative contrast factor are driven toward the pressure antinodes.

Based on these principles, formed elements of blood can be separated from capture particles (and thus the undesirable particles bound to the capture particles). For example, capture particles can be selected to have negative contrast factors, which is opposite to the positive contrast factors of the formed elements of blood. Thus, in response to the standing acoustic wave, the formed elements are driven towards the resulting pressure node while the capture particles are driven towards the antinodes.

As illustrated in the system 100, the cleansed blood exits the microfluidic flow chamber 108 at a first outlet 110. From there the blood is returned to the patient 101 via an intravenous supply line 111. In some implementations, the blood in the supply line 111 is reheated to body temperature before returning to the patient 101. In other implementations an infusion pump is used to return the blood to the patient 101, while in the system 100 the pressure generated in the system by pumps 103 and 106 is adequate to force the blood to return to the patient 101.

As illustrated in the system 100, waste material (e.g. the capture particle and undesirable particles) exit the microfluidic flow chamber 108 and enter a waste collection unit 113. In some implementations, the waste collection unit 113 contains a capture particle recycler. The capture particle recycler unbinds the undesirable particles from the capture particles. The capture particles are then returned to the reservoir 115 via tubing 114. The undesirable particles are then disposed of. In some implementations, the undesirable particles are saved for further testing.

In some implementations, the microfluidic flow chamber 108 can be used for other methods than blood cleansing such as, but not limited to, apheresis and analytical sample preparation. For example, in an apheresis process cells, blood plasma, or other waste is removed from the blood and discarded. A replacement fluid or suspension can be added back to the blood to replace the volume lost from the removal of the waste. In an example where the microfluidic flow chamber 108 is used for sample preparation, the microfluidic flow chamber 108 can be used to flow extract a desired fraction of cells or particles from a sample or to remove particles or cells to leave purified liquid fraction.

While the system 100 is described above for the in-line cleansing of a patient's blood, in alternative implementations, the system 100 can be used to cleanse stored blood or other stored fluids. For example, the system 100 can be used to cleanse collected blood for later infusion to help ensure the safety of the blood or it can be used to prepare blood for analysis.

Figure 2A:
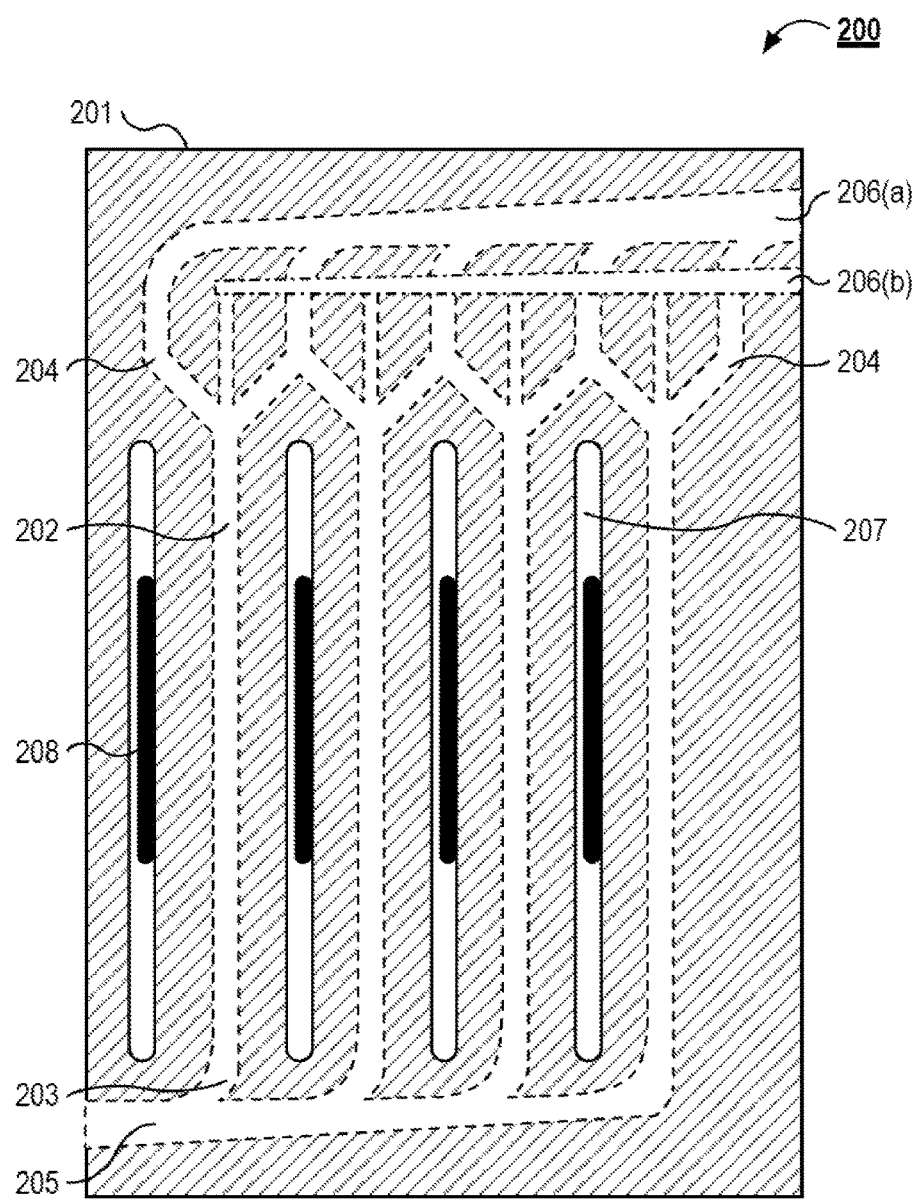
FIG. 2A illustrates a top view schematic of an example microfluidic flow chamber as can be used in the system illustrated in FIG. 1.

FIG. 2A illustrate a top view schematic of an example microfluidic flow chamber 200 as can be used in the system 100 illustrated in FIG. 1. The microfluidic flow chamber 200 includes a substrate 201. The substrate 201 defines a plurality of separation channels 202. Each of the separation channels 202 includes an inlet 203 and multiple outlets 204. Each inlet 203 is coupled to a feed channel 205, and each of the outlets 204 are coupled to a collection channel 206. As illustrated, the microfluidic flow chamber 200 includes a first collection channel 206(a) and a second collection channel 206(b). The substrate 201 also defines a plurality of isolation slots 207. The acoustic transducers 208 protrude from a base substrate (not shown) below the substrate 201 and project through isolation slots 207.

The substrate 201 defines the separation channels 202 and the isolation slots 207. In some implementations, the substrate 201 includes rigid materials such as silicon, glass, metals, or other materials that establish a high acoustic contrast between the fluid flowing though the separation channels 202 and the substrate 201. In other implementations, the substrate 201 includes relatively more elastic materials, which establish a lower acoustic contrast between the fluid flowing the separation channels 202 and the substrate 201. These materials can include thermoplastics, such as, polystyrene, acrylic (polymethylmethacrylate), polysulfone, polycarbonate, polyethylene, polypropylene, cyclic olefin copolymer, silicone, liquid crystal polymer, and polyvinylidene fluoride.

The substrate 201 of the microfluidic flow chamber 200 includes multiple separation channels 202. The separation channels 202 are formed into an array of separation channels 202. The array of separation channels 202 can include between about 2 and about 50, between about 10 and about 40, or between about 20 and about 30 separation channels. The inlet 203 of each of the separation channels 202 is coupled to the feed channel 205 that provides fluid to each of the separation channels 202. The feed channel 205 and the separation channels 202 can be configured in a trunk and branch configuration. For example, as illustrated in FIG. 2A, the feed channel 205 can narrow as separation channels 202 branch off the feed channel 205. The trunk and branch configuration can also include smooth and gradual transitions between the feed channel 205 and each of the separation channels 202. The transitions between the feed channel 205 and the separation channels 202 are configured to reduce or prevent damage to blood flowing through the microfluidic flow chamber 200 and to prevent clotting. The feed channel 205 receives fluid from the manifold system described herein. The separation channels 202 are configured to branch into multiple outlets 204 toward their downstream end. As illustrated, the separation channels 202 include a central outlet and two lateral outlets (generally referred to as outlets 204). The two lateral outlets of each separation channel 202 are coupled to the collection channel 206(a), and the central outlet of each separation channel 202 is couple to the collection channel 206(b). As with between the feed channel 205 and the separation channels 202, the transitions between the separation channels 202 and the collection channels 206(a) and 206(b) are smooth and gradual.

In some implementations, the capture particles are aligned toward an aggregation axis that is along a central axis of each of the separation channels. In these implementations, the fluid flowing into the central outlet 204 is enriched with the capture particles, and the fluid flowing into the lateral outlets 204 is depleted of the capture particles. In other implementations, the capture particles are aligned toward the walls of each of the separation channels 202 by the acoustic transducers 208. In these implementations, the fluid flowing into the lateral outlets 204 is enriched with the capture particles and the fluid flowing into the central outlet 204 is depleted of the capture particles.

As illustrated in FIG. 2A, the collection channel 206(b) is in a different plane than the separation channels 202 and the collection channel 206(a). The collection channel 206(b) is coupled to each of the central outlets 204 by a fluidic via between the plane of the separation channels 202 and the collection channel 206(b). In some implementations, the collection channel 206(b) is in the same plane as the central outlets 204 and the collection channel 206(a) is in a different plane than the lateral outlets 204 and separation channels 202.

The microfluidic flow chamber 200 illustrated in FIG. 2A also includes a plurality of isolation slots 207. The isolation slots 207 are channels that run parallel to the separation channels 202. The isolation slots 207 have a height equal to the thickness of the substrate 201 and form air gaps through the substrate 201 between adjacent separation channels 202. For example, the isolation slots 207 can be milled or cut through the substrate 201. The air gaps between the adjacent separation channels 202, as provided by the isolation slots 207, isolate the acoustic effects of waves from the acoustic transducers 208 to specific separation channels 202.

In some implementations, the isolation slots 207 run substantially the entire length of the separation channels 202, and in other implementations, the isolation slots 207 run along a length of the separation channels 202 only near the acoustic transducers 208. The isolation slots 207 are between about 100 µm and about 5 mm, between about 500 µm and about 4 mm, between about 1 mm and about 3 mm, or between about 1 mm and about 2 mm wide. The separation channels 202 are between about 1 cm and about 10 cm, about 2 cm and about 8 cm, or about 4 cm and about 6 cm long.

A plurality of acoustic transducers 208 coupled to the microfluidic flow chamber 200. The acoustic transducers 208 are, for example, piezoelectric transducers as described above in relation to FIG. 1. Each of the acoustic transducers 208 are configured to imposes a standing acoustic wave on one of the separation channels 202 of the microfluidic flow chamber 200. The standing acoustic wave is applied transverse to the flow of the fluid through the separation channels 202. The standing acoustic waves generate pressure nodes and pressure antinodes within the separation channels 202 that drive the capture particles towards or away from the walls of the separation channels 202 or toward other aggregation axes. The acoustic wave may be applied continuously or intermittently.

Figure 2B:
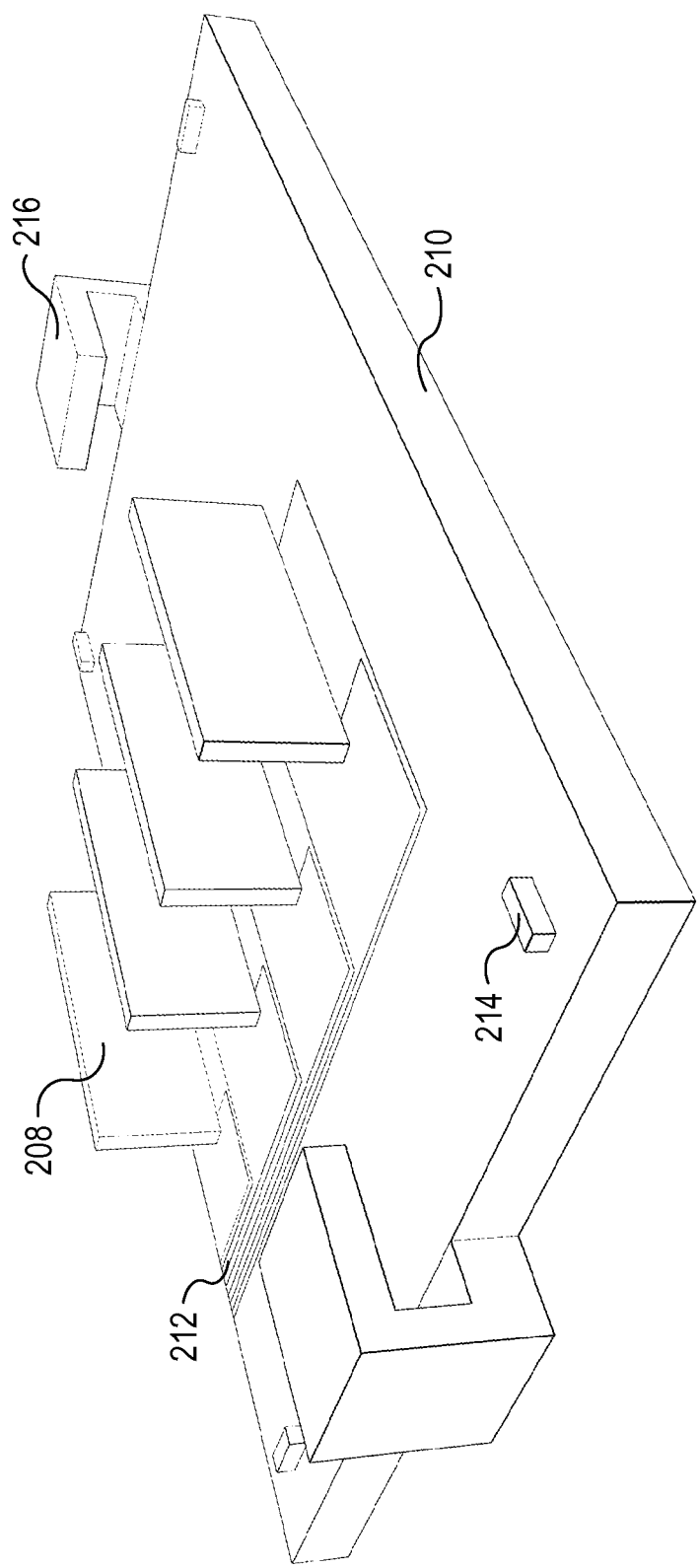
FIG. 2B illustrates an isometric view of an example base substrate to which the microfluidic flow chamber illustrated in FIG. 2A is be coupled.

FIG. 2B illustrates an isometric view of an example base substrate 210 to which the microfluidic flow chamber 200, illustrated in FIG. 2A, can be coupled. The base substrate 210 includes the acoustic transducers 208, which are powered via electrical traces 212. The base substrate 210 includes a plurality of orientation markers 214. The base substrate 210 also include clamps 216 to clamp a microfluidic flow chamber to the base substrate 210.

The acoustic transducers 208 are mounted to the base substrate 210. The acoustic transducers 208 project perpendicular to the base substrate 210. As illustrated in FIG. 2A, when the microfluidic flow chamber 200 is coupled to the base substrate 210 each of the acoustic transducers 208 project into one of the isolation slots 207. The acoustic transducers 208 are coupled to one the walls of the of the isolation slots 207, which is a shared wall with one of the adjacent separation channels 202. For example, the acoustic transducers 208 can be coupled to the inner walls of the isolation slots 208 by glycerol, glue, film, gel, or other material configured to efficiently transfer waves from the acoustic transducers 208 to the inner wall of the isolation slots 207.

The base substrate 210 includes a plurality of electrical traces 212. The electrical traces 212 provide power to and ground each of the acoustic transducers 208. In some implementations, the electrical traces 212 terminate in a multi-pin electrical connector that enable each of the acoustic transducers 208 to be controlled independently of one another.

The base substrate 210 also includes a plurality of orientation markers 214. The orientation markers 214 are raised protrusions positioned towards each of the corners of the base substrate 210. The bottom of the substrate 201 illustrated in FIG. 2A includes recesses that mate with each of the orientation markers 214. The orientation markers 214 can ensure the substrate 201 is properly aligned with the base substrate 201—therefore ensuring the acoustic transducers 208 are properly aligned with the separation channels 202.

The base substrate 210 also includes clamps 216. As illustrated, the clamps 216 are illustrated in their closed (or clamped) position. Once the substrate 201 is placed on the base substrate 210 and properly orientated using the orientation markers 214, the clamps 216 are closed to reversibly couple the substrate 201 to the base substrate 210. In some implementations, the base substrate 210 includes a clamp 216 on each of its four sides rather than just two sides as illustrated in FIG. 2B.

Figure 2C:
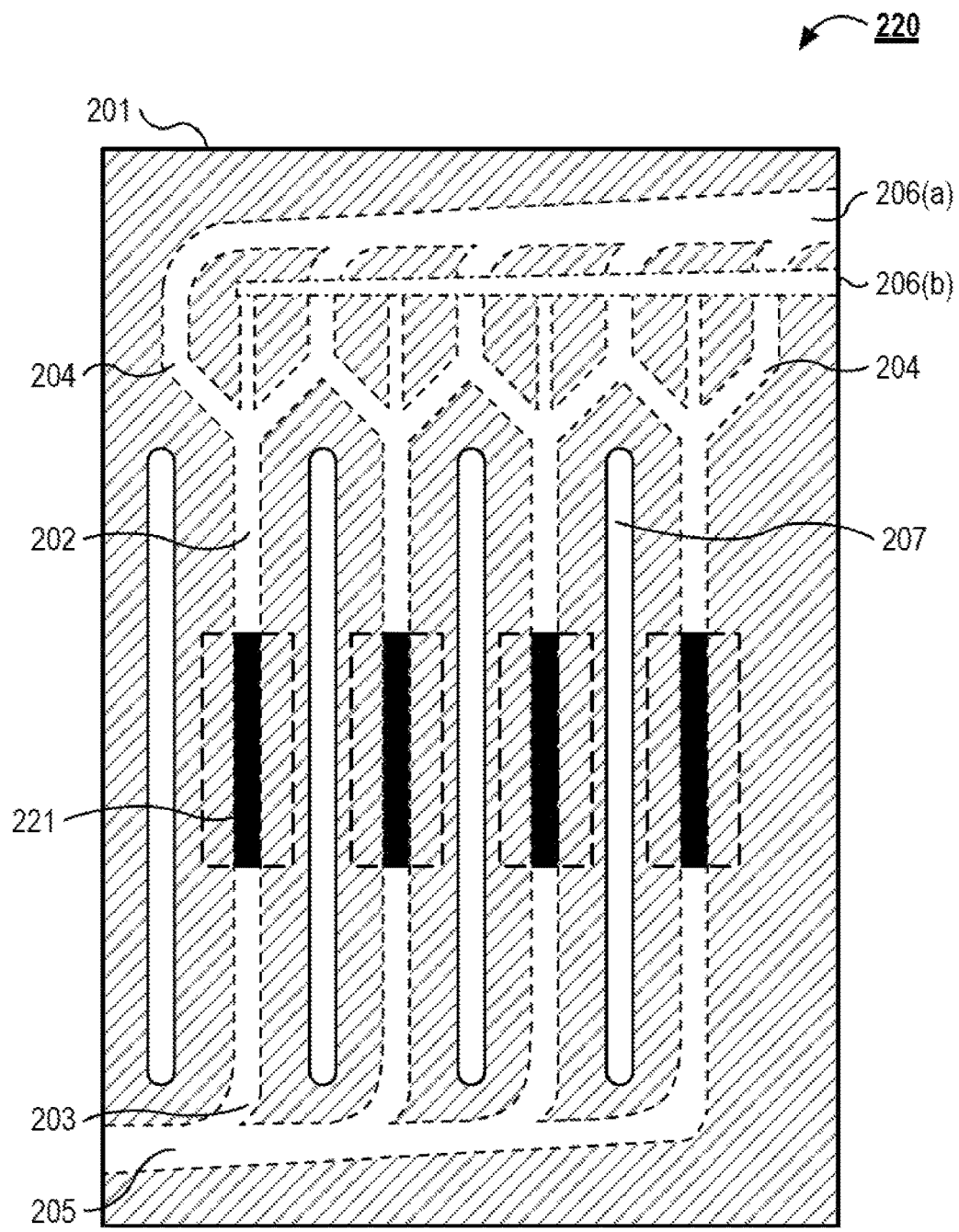
FIG. 2C illustrate a top view schematic of another example microfluidic flow chamber as can be used in the system illustrated in FIG. 1.

FIG. 2C illustrates a top view of an example microfluidic flow chamber 220. As described above in relation to FIG. 2A, the microfluidic flow chamber 220 includes a substrate 201. The substrate 201 defines a plurality of separation channels 202. Each of the separation channels 202 includes an inlet 203 and multiple outlets 204. Each inlet 203 is coupled to a feed channel 205, and each of the outlets 204 are coupled to a collection channel 206. As illustrated, the microfluidic flow chamber 200 includes a first collection channel 206(a) and a second collection channel 206(b). The substrate 201 also defines a plurality of isolation slots 207. The microfluidic flow chamber 220 also includes acoustic transducers 221. As described below in relation to FIG. 2D, the acoustic transducers 221 lie flat on a base substrate (not shown) below the substrate 201. The acoustic transducer 221 are coupled to a bottom wall of each of the separation channels 202.

Figure 2D:
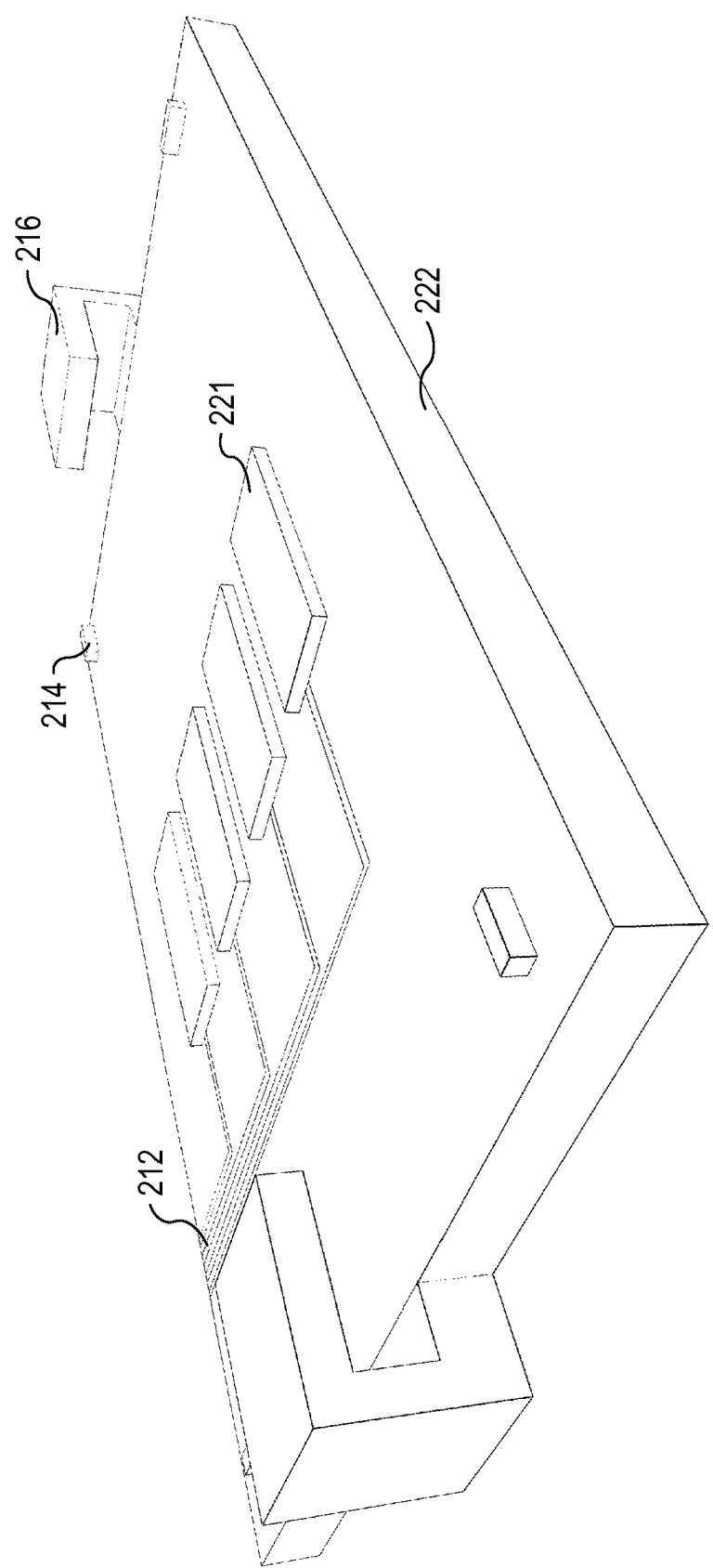
FIG. 2D illustrates an isometric view of an example base substrate to which the microfluidic flow chamber illustrated in FIG. 2C is be coupled.

FIG. 2D illustrates an isometric view of an example base substrate 222 to which the microfluidic flow chamber 220, illustrated in FIG. 2C, is coupled. The base substrate 222 includes the acoustic transducers 221, which are powered via the electrical traces 212. The base substrate 222 includes a plurality of orientation markers 214. The base substrate 222 also include claims 216 to clamp a microfluidic flow chamber to the base substrate 210. The clamps 216, orientation markers 214, and electrical traces 212 can be similar to those described above. The acoustic transducers 221 lie flat on the base substrate 222 and are configured to project an acoustic wave upward into the separation channels 202 of the microfluidic flow chamber 220. In some implementations, the microfluidic flow chamber 220 includes recesses to receive the acoustic transducers 221, enabling the acoustic transducers 221 to provide an orientation function similar to the orientation markers 214. In some implementations, a single, larger acoustic transducer 221 is coupled to the base substrate 222 rather than a plurality of smaller acoustic transducers 221.

Figure 3:
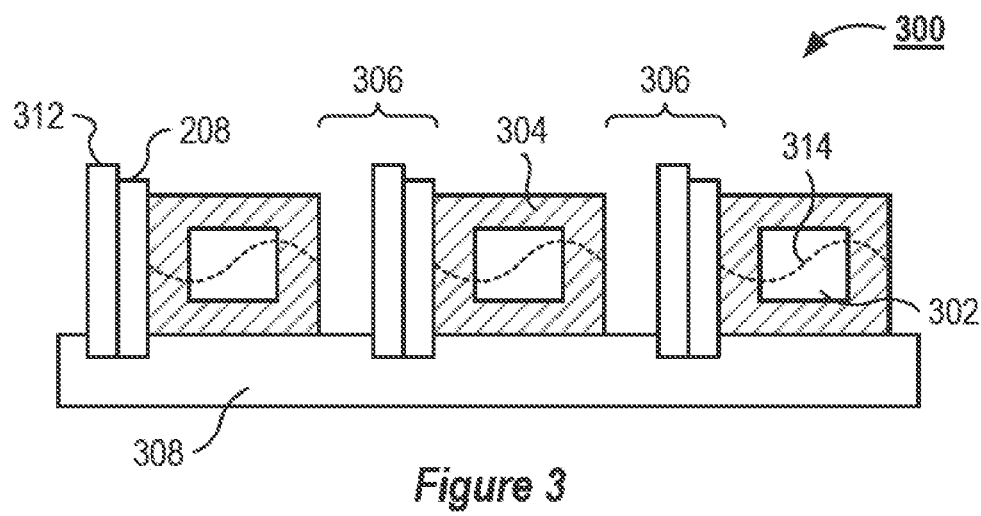
FIG. 3 illustrate a cross-sectional view of an example microfluidic flow chamber as can be used in the system illustrated in FIG. 1.

FIG. 3 illustrates a cross-sectional view of an example microfluidic flow chamber 300. The microfluidic flow chamber 300 includes three separation channels 302 that are defined within a plastic substrate 304. Each adjacent separation channel 302 is separated by an isolation slot 306. The substrate 304 that defines the separation channels 302 and the isolation slots 306 sits atop a base substrate 308. An acoustic transducer 208 is coupled to an inner wall of each of the isolation slots 306. A heat sink 312 is coupled to each of the acoustic transducers 208.

The base substrate 308 of the microfluidic flow chamber 300 is an acoustically inactive substrate. For example, the base substrate 308 does not substantially transmit waves generated by the acoustic transducers 208. The acoustic transducers 208 and the heat sinks 312 are coupled to the base substrate 308. The base substrate 308 can also include electrical traces for powering the acoustic transducers 208. In some implementations, the base substrate 308, with its associated acoustic transducers 208 and heat sinks 312, is reusable and the microfluidic flow chamber 300 is disposable.

As illustrated in FIG. 3, the acoustic transducers 208 are coupled to the right inner wall of the isolation slots 306. In the microfluidic flow chamber 300, each acoustic transducers 208 applies a standing wave 314 to the separation channel 302 to the right of the acoustic transducer 208. The standing wave 314 travels from the acoustic transducer 208, through the portion of the substrate 304 defining the left wall of the separation channel 302, into the separation channel 302, and then into the portion of the substrate 304 defining the right wall of the separation channel 302. As illustrated, the isolation slots 306 substantially fail to transmit the standing wave 314, which prevents the standing wave 314 from meaningfully effecting adjacent separation channels 302.

The microfluidic flow chamber 300 can be coupled to the base substrate 308 by glue or by mechanically coupling the microfluidic flow chamber 300 to the base substrate 308. For example, the microfluidic flow chamber 300 can be clamped to the base substrate 308. In some implementations, the base substrate 308 and the microfluidic flow chamber 300 include registration features that help properly position the substrate 304 on the base substrate 308.

The heat sinks 312 of the microfluidic flow chamber 300 are configured to dissipate heat generated by the acoustic transducers 208. For example, the heat sinks 312 are configured to dissipate enough heat to prevent the acoustic transducers 208 from warming fluids flowing through the separation channels 302. In some implementations, the heat sinks 312 are, or include, thermoelectric coolers. In some implementations, the base substrate 308 includes fluidic lines that flow into the heat sinks 312 to provide fluidic cooling to the heat sinks 312.

FIGS. 4A and 4B illustrate cross-sectional views of example microfluidic flow chambers. FIG. 4A illustrates a cross-sectional view of an example microfluidic flow chamber 400 with symmetrical walls, and FIG. 4B illustrates a cross-sectional view of an example microfluidic flow chamber 450 with asymmetrical walls. In some implementations, asymmetrical walls refer to opposite walls of the separation channels having different thicknesses. FIG. 4A illustrates a single separation channel 401, which may be one of an array of separation channels, as described above in relation to FIG. 2A. The separation channel 401 is defined by a cover sheet 402 sitting atop a channel layer 403. The cover sheet 402 is coupled to the channel layer 403, which is coupled to a base substrate 404. As described above, an acoustic transducer 208 is coupled to an inner wall of a isolation slot and applies a standing wave 405 to the separation channel 401.

The channel layer 403 and cover sheet 402 of the separation channel 401 are manufactured from, and without limitation, polystyrene, glass and polyimide, polyacrylic, polysulfone, silicon, polystyrene, acrylic (polymethylmethacrylate), or other materials. In some implementations, the channel layer 403 is manufactured by milling, embossing, and/or etching. After creating the two layers, the two layers are joined together by thermocompression, mechanical clamping, adhesive bonding, and/or plasma bonding. The acoustic transducer 208 imparts the standing wave 405 at a specific wavelength ($\lambda$) across the separation channel 401. The dimensions of the channel layer 403, cover sheet 402, and separation channel 401 are dependent on the selected wavelength ($\lambda$), as described below.

As described above, in some implementations, the substrate sheet is relatively elastic (e.g., when a polystyrene or acrylic material is used), which provides a relatively lower acoustic contrast between the fluid flowing through the separation channel 401 and the walls of the channel layer 403. The relatively elastic materials can form a poor resonator. In implementations using relatively more elastic materials, the frequency f of the standing wave 405 is equal to $c_{Fluid}/2w$, where $c_{Fluid}$ is the speed of sound in the fluid flowing through the separation channel 401 and w is the width of the wall. The wall width w is calculated using the shear speed of sound in the wall material $c_s(f)$, which is different than the bulk longitudinal velocity of sound through the material $c_p$. The shear speed of sound in the wall material $c_s(f)$ is frequency dependent. In these implementations, the wall width is $w=c_s(f)/4f$.

In other implementations, where the material of the substrate is less elastic and forms a good acoustic resonator, the thickness of the side wall is equal to $c_{wall}/4f$, where $c_{wall}$ is wall the speed of sound in the wall material. The $c_{wall}$ for the material is equal to the bulk longitudinal velocity of sound through the material $c_p$. In some implementations, odd multiples of the calculated wall thickness may be used. The width of the separation channel 401 is equal to about half the wavelength of the standing wave 405 in the fluid ($\lambda_{fluid}/2$).

When the standing wave 405 reaches the interface between the fluid in the separation channel 401 and the material of the channel layer 403, the wave splits into a transmitted and reflected portion. When the acoustic contrast is large between the fluid and material, the majority of the standing wave 405 is reflected due to the large difference in acoustic impedance, and the majority of the acoustic energy remains confined in the channel layer 403. The reflected portion of the standing wave redistributes itself to a longitudinal wave and a shear wave (or lamb wave).

In examples where the substrate is formed from a relatively more elastic material, the bulk longitudinal velocity of sound through the material $c_p$ is greater than the speed of sound through the fluid $c_{fluid}$, which is greater than speed of the reflected wave $c_s$. In these examples, the acoustic impedance mismatch between the shear wave and the longitudinal wave is small, which enables the standing wave 405 to be transferred from the channel layer 403 to the separation channel 401 with minimal loss of energy.

As an example and comparison between designs employing a weak resonator material and a strong resonator material, assume the substrate is formed from silicon and the separation channel is filled with water. In this example, assuming the speed of sound in water is about 1460 m/s and the acoustic transducer 208 is operated at about 1.7 MHz, the width of the separation channel would be about 0.4 mm and the wall thickness (based on a speed of sound in silicon of about 5968 m/s) would be 0.88 mm. When using a weak resonator material, such as polystyrene, the separation channel would be about 0.4 mm, but the wall thickness would be about 1.05 mm (based on a speed of sound in polystyrene of about 1120 m/s) and the transducer 208 is operated at about 1.0 MHz.

FIG. 4B illustrates a single separation channel 451, which may be one of an array of separation channels, as described above in relation to FIG. 2A. The separation channel 451 is defined by a cover sheet 452 sitting atop a channel layer 453. The cover sheet 452 is coupled to the channel layer 453, which is coupled to a base substrate 404. As described above, an acoustic transducer 208 is coupled to an inner wall of an isolation slot and applies a standing wave 405 to the separation channel 451. As illustrated, the separation channel 451 is formed off-center with respect to the channel layer 453, which forms asymmetrically thick walls on either side of the separation channel 451. As illustrated, the thicker wall is adjacent to the acoustic transducer 208. In other implementations, the thinner wall can be adjacent to the acoustic transducer 208.

In some implementations, a microfluidic flow chamber with asymmetrical walls is formed in a substrate that has a relatively low acoustic impedance compared to the fluid flowing through the separation channels because it is important that the wave transfer between the wall material and fluid with relatively little energy loss. For example, the substrate is relatively more elastic (e.g., includes polystyrene or acrylic) than compared to silicon, glass, or a metal.

In some implementations, forming the microfluidic flow chamber 450 with asymmetrical walls enables the capture particles to be focused along an arbitrary axis of the separation channel 451. This is in contrast to implementations with symmetrical walls where the capture particles can be aligned with an axis in the center of the separation channel 401 or along the walls of the separation channel 401. In one example, the channel 451 dimensions and channel layer 453 width are calculated as described above with respect to the device with symmetrical walls, but one of the sidewalls is thicker than the other by a length equal to ¼ of the width of channel 451. In some implementations, the thicknesses of each of the walls is determined through numerical simulation.

In some implementations of the microfluidic flow chamber 450 with asymmetrical walls, the thicker wall has a thickness of about $c_w/4f+d$, and the thinner wall has a thickness of about $c_w/4f-d$. The lateral width of the separation channel is about $c_f/2f$. When calculating the thickness of the thicker and thinner wall $c_w$ is the acoustic velocity of an acoustic wave in the wall material (or an odd multiple thereof), $c_f$ is the acoustic velocity of the acoustic wave in the fluid, f is the desired operating frequency of the acoustic wave, and d is a width increment defined by $c_f/16f<d<c_f/4f$. In some implementations, f is multiplied by a factor of between about 1.5 and about 2.5, between about 1.5 and about 2, or about 1.7.

Figure 5:
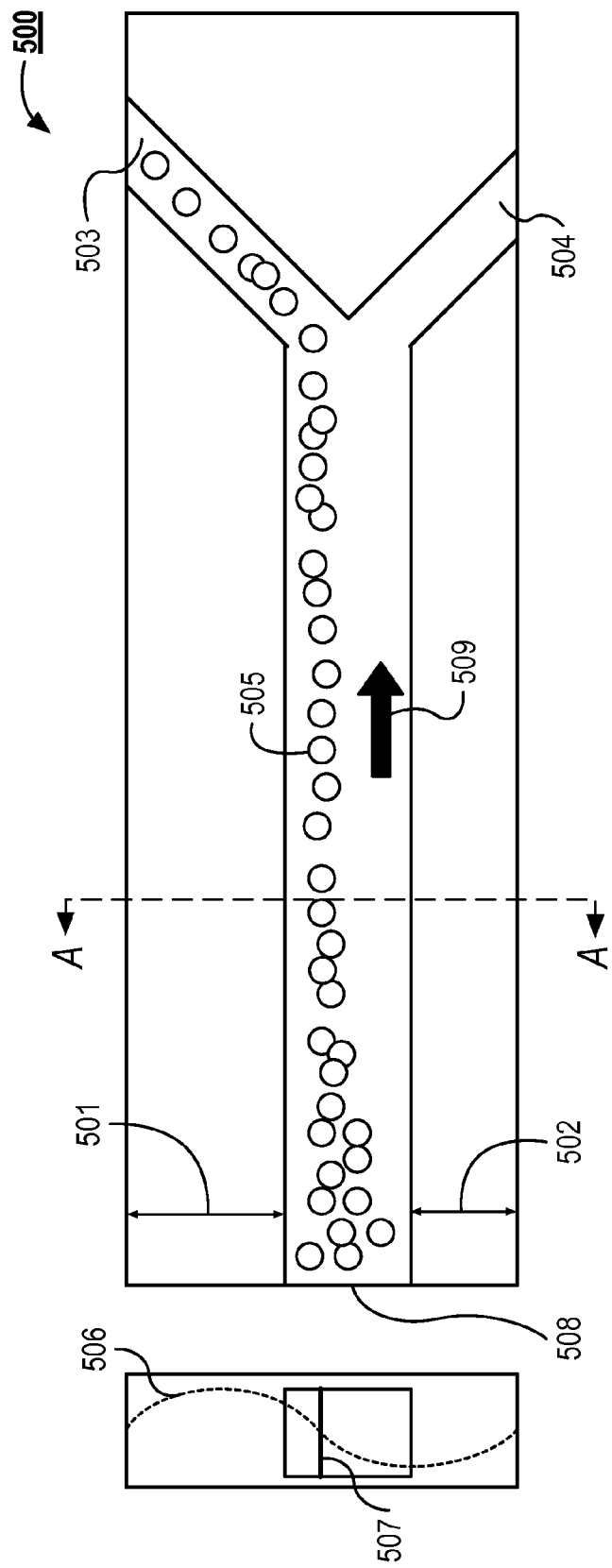
FIG. 5 illustrates a top view and cross-sectional view of an example microfluidic flow chamber with asymmetrical walls as can be used in the system illustrated in FIG. 1.

FIG. 5 illustrates a top view of an example separation channel 500 and a cross-sectional view of the separation channel 500 made along cut line A-A. The separation channel 500 includes asymmetrical walls, where wall 501 is thicker than wall 502. The separation channel 500 includes an inlet 508, a first outlet 503 and a second outlet 504. A plurality of capture particles 505 flow down the separation channel 500 in a direction 509 from the inlet 508 to the first and second outlets 503 and 504. A standing wave 506 is applied to the separation channel 500 forming an aggregation axis 507. In some implementations, the above described devices that include arrays of separation channels can include arrays of separation channels with asymmetrical walls.

The capture particles 505 align at the aggregation axis 507. The aggregation axis 507 can be formed at a pressure node or pressure antinode of the standing wave 506. As described in relation to FIG. 2A, devices with symmetrical walls include three outlets to collect the separated contents of a fluid. For example, a device with symmetrical walls may align the capture particle toward the center of the separation channel. A capture particle dense fluid would then flow into a central outlet of the device, and a capture particle depleted fluid would slow into the two lateral outlets. However as described below in relation to FIG. 5, a device with asymmetrical walls, can be less complex because the separation channels can include only two outlets.

As illustrated in FIG. 5, using an asymmetrical wall design, the aggregation axis 507 is created between the central axis of the separation channel's lumen and the face of the wall 501 of the separation channel 500. As illustrated in FIG. 5, the aggregation axis 507 is generated toward the wall 501; however, the thicknesses of the walls 501 and 502 can be adjusted to place the aggregation axis 507 at any location in the separation channel 500. In this example, the capture particle dense fluid can be collected with a first outlet 503 and the capture particle depleted fluid is collected with the second outlet 504.

As illustrated, the first outlet 503 and the second outlet 504 are substantially the same size. In other implementations, the first outlet 503 and the second outlet 504 are sized differently. For example, the aggregation axis 507 can be placed closer to the wall 501, enabling the first outlet 503 to be smaller than the second outlet 504.

Figure 6:
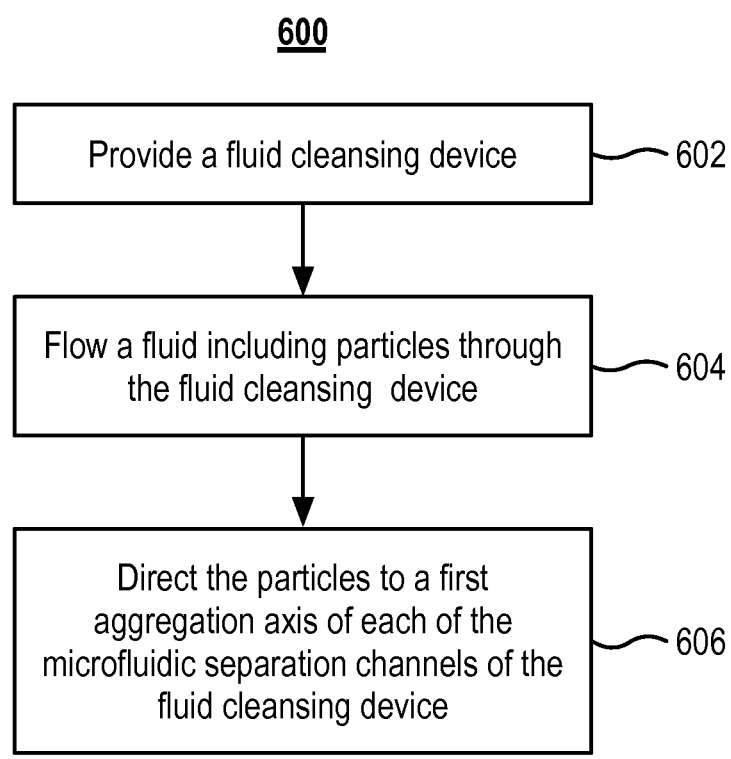
FIG. 6 illustrates a flow chart of an example method of cleansing a fluid using the system illustrated in FIG. 1.

FIG. 6 illustrates a flow chart of an example method 600 of cleansing a fluid. The method 600 includes providing a fluid cleansing device (step 602). A fluid containing capture particles is flowed through the fluid cleansing device (step 604). The capture particles are directed toward a first aggregation axis in each of the separation channels of the fluid cleansing device (step 606).

As set forth above, the method 600 includes providing a fluid cleansing device (step 602). The fluid cleansing device can include any of the microfluidic flow chambers described herein. Also with reference to FIG. 2A, the fluid cleansing device includes substrate 201 that defines an array of separation channels 202. Each of separation channels 202 includes an inlet 203 at an upstream portion and two or more outlets 204 at a downstream portion of the separation channel 202. Each of the adjacent separation channels 202 are separated from one another by an isolation slot 207. An acoustic transducer 208 is positioned within each of the isolation slots 207 and directs a standing acoustic wave toward a different one of the separation channels 202.

The method 600 also includes flowing a fluid through the fluid cleansing device (step 604). In some implementations, capture particles are mixed into the fluid before the fluid flows through the fluid cleansing device. The capture particles are configured to be acoustically mobile in the presence of a standing wave (e.g., the standing wave drives the capture particles to pressure node or pressure antinode). The acoustic mobility of the capture particles is tuned by configuring the capture particles to have a specific size, density, or compressibility. In some implementations, the capture particles are configured to be substantially more or substantially less acoustically mobile than other particles in the fluid. In some implementations, the capture particles include affinity particles anchored to the outer surface of the capture particles. The affinity particles are configured to bind to toxins, pro-inflammatory cytokines, bacteria, viruses, or specific cell types. In some implementations, cells, such as red blood cells, are acoustically mobile and may be driven to an aggregation axis without the use of capture particles.

The method 600 also includes directing the capture particles toward a first aggregation axis in each of the separation channels of the fluid cleansing device (step 606). Also with reference to FIGS. 2A-5, each of the acoustic transducers 208 generate a standing acoustic wave within a respective separation channel. The standing waves forms pressure nodes and/or pressure antinodes within the separation channel, which form aggregation axis along the length of the separation channel. As illustrated in FIG. 5, the capture particles are directed toward the aggregation axis 507 by the standing wave 506. The aggregation axis 507 is aligned with the first outlet 503. As the fluid travels down the separation channel, the capture particles 505 align with the aggregation axis 507 and flow out the first outlet 503. Simultaneously, capture particles depleted fluid flows out the second outlet 504.

In an example where the capture particles include affinity particles that bind to a toxin, the capture particles can be mixed with a patient's blood. The capture particles will bind to the toxin in the patient's blood. As the capture particles flow down the separation channel, the capture particles, with their bound toxins, exit the fluid cleansing device at outlet 503. Blood substantially free of toxin exits the fluid cleansing device at outlet 504 and can be returned to the patient. In some implementations, the capture particles exiting the outlet 503 can be further processed to separate the capture particles (and toxins) from the blood flowing out the first outlet 503.

While the above method 600 is described in relation to cleaning a fluid, in some implementations, the method 600 can be used to enrich a fluid. For example, the capture particles may bind to desired particles (e.g., a specific type of cell), which can be directed toward an outlet and collected for further use.

The disclosed system and methods may be embodied in other specific forms without departing from the spirit or essential characteristics thereof. The forgoing implementations are therefore to be considered in all respects illustrative, rather than limiting of the invention.

The invention claimed is:

1. A separation device comprising:
 a plastic substrate defining:
  a plurality of microfluidic separation channels each having an upstream portion and a downstream portion, the upstream portion comprising an inlet and the downstream portion comprising at least a first outlet and a second outlet; and
  one or more isolation slots, one of the one or more isolation slots positioned between each of the plurality of microfluidic separation channels; and
 a base substrate coupled to the plastic substrate and comprising one or more acoustic transducers, each of the one or more acoustic transducers coupled to a wall of one or more of the respective plurality of microfluidic separation channels.

2. The device of claim 1, wherein each of the one or more acoustic transducers protrude perpendicular to a face of the base substrate and into a respective one of the one or more isolation slots.

3. The device of claim 1, wherein the first outlet of each of the plurality of microfluidic separation channels is positioned substantially along a longitudinal axis of the respective microfluidic separation channel.

4. The device of claim 1, wherein the second outlet of each of the plurality of microfluidic separation channels is positioned adjacent to a wall of the respective microfluidic separation channel.

5. The device of claim 1, wherein each of the plurality of microfluidic separation channels further comprise:
a first wall having a first thickness; and
a second wall opposite the first wall and having a second thickness.

6. The device of claim 5, wherein the first thickness and the second thickness are about equal to $c_s(f)/4f$, or an odd multiple thereof, where $c_s(f)$ is a frequency dependent speed of a shear wave through the plastic.

7. The device of claim 5, wherein the second thickness is different than the first thickness.

8. The device of claim 7, wherein the first thickness is about $c_w/4f+d$, the second thickness is about $c_w(f)/4f-d$, and a lateral width of each of the of microfluidic separation channels is about $c_f/2f$, where $c_w$ is an odd multiple of an acoustic velocity of an acoustic wave in the plastic substrate, $c_f$ is an acoustic velocity of the acoustic wave in a fluid flowing through each of the plurality of microfluidic separation channels, f is an operating frequency of the acoustic wave, and d is a width increment defined by $c_f/16f<d<c_f/4f$.

9. The device of claim 1, wherein each of one or more isolation slots run substantially parallel to and the entire length of the plurality of microfluidic separation channels.

10. The device of claim 1, wherein one or more isolation slots each have a height equal to a thickness of the plastic substrate.

11. The device of claim 1, further comprising a manifold configured to distribute a fluid to the inlet of each of the plurality of microfluidic separation channels.

12. The device of claim 11, wherein the manifold comprises a network of biomimetic channels.

13. A separation device comprising:
a first separation channel defined in a plastic substrate, the first separation channel having an upstream portion and a downstream portion;
the upstream portion comprising an inlet; and
the downstream portion comprising a first outlet positioned along a first wall and a second outlet positioned along a second wall, wherein the thickness of the first wall is different than the thickness of the second wall;
a second separation channel defined in the plastic substrate, the second separation channel adjacent to the first separation channel; and
an isolation slot defined in the plastic substrate, the isolation slot positioned between the second separaton channel and the first separation channel.

14. The device of claim 13, further comprising a base substrate coupled to the plastic substrate, the base substrate comprising an acoustic transducer.

15. The device of claim 13, wherein the first thickness is about $c_w/4f+d$, the second thickness is about $c_w/4f-d$, and a lateral width of each of the of microfluidic separation channels is about $c_f/2f$, where $c_w$ is an odd multiple of an acoustic velocity of an acoustic wave in the plastic substrate, $c_f$ is an acoustic velocity of the acoustic wave in a fluid flowing through each of the plurality of microfluidic separation channels, f is an operating frequency of the acoustic wave, and d is a width increment defined by $c_f/16f<d<c_f/4f$.

* * * * *